(12) United States Patent
Nitsche et al.

(10) Patent No.: US 10,283,002 B2
(45) Date of Patent: May 7, 2019

(54) APPARATUS, METHODS, AND SYSTEMS FOR TARGET-BASED ASSESSMENT AND TRAINING FOR ULTRASOUND-GUIDED PROCEDURES

(71) Applicant: Wake Forest University Health Sciences, Winston-Salem, NC (US)

(72) Inventors: Joshua F. Nitsche, Winston-Salem, NC (US); Brian C. Brost, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 186 days.

(21) Appl. No.: 14/683,722

(22) Filed: Apr. 10, 2015

(65) Prior Publication Data

US 2015/0294599 A1  Oct. 15, 2015

Related U.S. Application Data

(60) Provisional application No. 61/978,645, filed on Apr. 11, 2014, provisional application No. 61/984,401, filed on Apr. 25, 2014.

(51) Int. Cl.
*G09B 5/00* (2006.01)
*A61B 8/08* (2006.01)
*G09B 23/28* (2006.01)

(52) U.S. Cl.
CPC .............. *G09B 5/00* (2013.01); *A61B 8/0841* (2013.01); *G09B 23/286* (2013.01)

(58) Field of Classification Search
CPC ........ G09B 5/00; G09B 23/285; A16B 8/0841

USPC .......................................................... 434/262
See application file for complete search history.

(56) References Cited

U.S. PATENT DOCUMENTS

| 6,568,941 B1* | 5/2003 | Goldstein | G09B 23/28 434/262 |
| 2005/0181342 A1* | 8/2005 | Toly | G09B 23/285 434/262 |
| 2005/0214727 A1* | 9/2005 | Stoianovici | G09B 23/28 434/262 |

(Continued)

FOREIGN PATENT DOCUMENTS

| WO | WO 2012/096562 | 7/2012 |
| WO | WO 2012/123942 | 9/2012 |
| WO | WO 2013/076056 | 5/2013 |

OTHER PUBLICATIONS

Patent Cooperation Treaty, International Search Report and Written Opinion, International Application No. PCT/US2015/025357, dated Jun. 30, 2015.

*Primary Examiner* — Robert P Bullington
(74) *Attorney, Agent, or Firm* — Kilpatrick Townsend & Stockton LLP

(57) ABSTRACT

Ultrasound-guided needle procedures require skills that are challenging to master, especially considering the need to manipulate 3-D structures while observing 2-D images (or even 3-D images). A pre-clinical assessment and training apparatus, methods, and systems are described herein. Targeting tasks require participants to contact target models designed to test various skills. Performance is compared between those with experience in ultrasound-guided medical procedures and those without experience, using at least one targeting task likely to be beneficial for assessment.

12 Claims, 10 Drawing Sheets

(56) References Cited

U.S. PATENT DOCUMENTS

| | | | |
|---|---|---|---|
| 2008/0293029 A1* | 11/2008 | Wilkins | G09B 23/286 434/272 |
| 2009/0142741 A1 | 6/2009 | Ault et al. | |
| 2009/0208915 A1* | 8/2009 | Pugh | G09B 23/30 434/267 |
| 2010/0041005 A1 | 2/2010 | Campbell et al. | |
| 2013/0337425 A1* | 12/2013 | Allen | G09B 23/281 434/268 |
| 2014/0004488 A1* | 1/2014 | Tepper | G09B 23/286 434/219 |

* cited by examiner

APPARATUS, METHODS, AND SYSTEMS FOR TARGET-BASED ASSESSMENT AND TRAINING FOR ULTRASOUND-GUIDED PROCEDURES

RELATED APPLICATIONS

The present application claims priority to U.S. Provisional Patent Application No. 61/978,645, filed Apr. 11, 2014 and to U.S. Provisional Patent Application No. 61/984,401, filed Apr. 25, 2014. The disclosures of U.S. Provisional Patent Application Nos. 61/978,645 and 61/984,401 are hereby incorporated by reference in their entirety herein.

FIELD

This invention relates to assessment and training of medical personnel for hand-eye coordination in performing ultrasound-guided procedures.

BACKGROUND

At present, training of medical professionals in ultrasound-guided procedures often occurs in a clinical environment. This approach has several disadvantages. It places the learner in the uncomfortable position of performing their initial procedures in an unfamiliar clinical setting where technical problems can have serious consequences for the patient. In addition, clinical training opportunities in some disciplines are limited.

The current training paradigm has been upheld in the past because there were no other viable alternatives. Alternatively simulators available for many of the ultrasound-guided needle procedures commonly used today are often highly specific to particular anatomical structures and therefore limited in use. Moreover, ongoing medical advances will likely lead to development of additional ultrasound-guided procedures not yet implemented in practice, such that a generalized training in the use of ultrasound-guided imaging to improve hand-eye coordination is beneficial for the development and training of existing and new applications. Depth perception, for example, is universally difficult to master while observing a 2-dimensional image, and practice on a system that broadly replicates the challenges of using ultrasound guidance to perform procedures may improve the skill and confidence of the user. Thus, there is a need for generalized assessment and training for skill in using ultrasound guidance for medical procedures. The present invention addresses this need.

Thus, there is a need for a generalized ultrasound-guided skill assessment and training apparatus and system, as well as methods for assessing skill in using ultrasound-guided imaging for procedures, as are described herein. Further provided are computer readable media for assessing skill in ultrasound-guided procedures involving a needle or other user-held devices or instruments.

SUMMARY

The present invention relates to an apparatus, methods, and systems for assessing and training users (e.g., clinicians or pre-clinical trainees) in ultrasound-guided procedures, and especially those procedures requiring manipulation of a needle, probe, guide wire, or other instrument.

In some embodiments, the invention comprises an apparatus for ultrasound-guided procedure assessment and/or training, comprising: a 3-dimensional (3-D) target model component having a plurality of points of contact and access to the points of contact. In some embodiments, the target model component comprises structures positioned at multiple angles. In some embodiments, the target model component mimics common anatomical structures and/or geometric access observed in ultrasound-guided procedures. In some embodiments, the apparatus further comprises a chamber component comprising the 3-D target model component and an opaque access surface for contact with an ultrasound imaging system. In some embodiments, the apparatus further comprises a needle, probe, guide wire, catheter, drain tube, or other user-held instrument component for performing tasks related to the target model component. The apparatus may further include an ultrasound imaging component for visualizing in 2 dimensions or 3 dimensions the target model components and the needle or other user-held device component via ultrasound probe contact with the chamber access surface.

In other embodiments, the invention comprises a method for assessing skill in ultrasound-guided procedures, comprising: providing an apparatus of the invention as described herein; assigning a user a task related to the 3-D target model component; and having the user perform the assigned task while visualizing the target model component and the needle or other user-held instrument via the ultrasound imaging system. The method may further comprise assigning the user a plurality of tasks related to the target model component. The method may further comprise timing successful performance of the assigned tasks. The method may further comprise comparing the performance of the user to that of experienced and inexperienced clinicians using the same apparatus.

In other embodiments, the invention comprises a method for assessment and/or training in ultrasound-guided procedures, comprising: providing an apparatus of the invention as described herein; and assigning a user a specific task related to a 3-D target model component. The method may further comprise having the user practice performing the assigned task while visualizing the target model component and the needle or other user-held component via an ultrasound imaging system. The method may further comprise assessing and timing user performance of the assigned task. The method may further comprise assigning the user a plurality of tasks related to the target model component.

In other embodiments, the invention comprises a system for ultrasound-guided procedure assessment and training, comprising: at least one 3-D target model component; a chamber component for enclosing the 3-D target model component, wherein the chamber comprises the target model component and an opaque access surface for contact with an ultrasound imaging system. The system may further comprise at least one of a needle, a probe, or other user-held component for performing tasks related to the target model component and/or an ultrasound imaging system component for visualizing the target model component and the needle or other user-held device component via ultrasound probe contact with the access surface. In some aspects, the system may also comprise a tool for objective assessment of skill level.

BRIEF DESCRIPTION OF THE FIGURES

The present invention may be better understood by referring to the following non-limiting figures.

DETAILED DESCRIPTION

Figure 1:
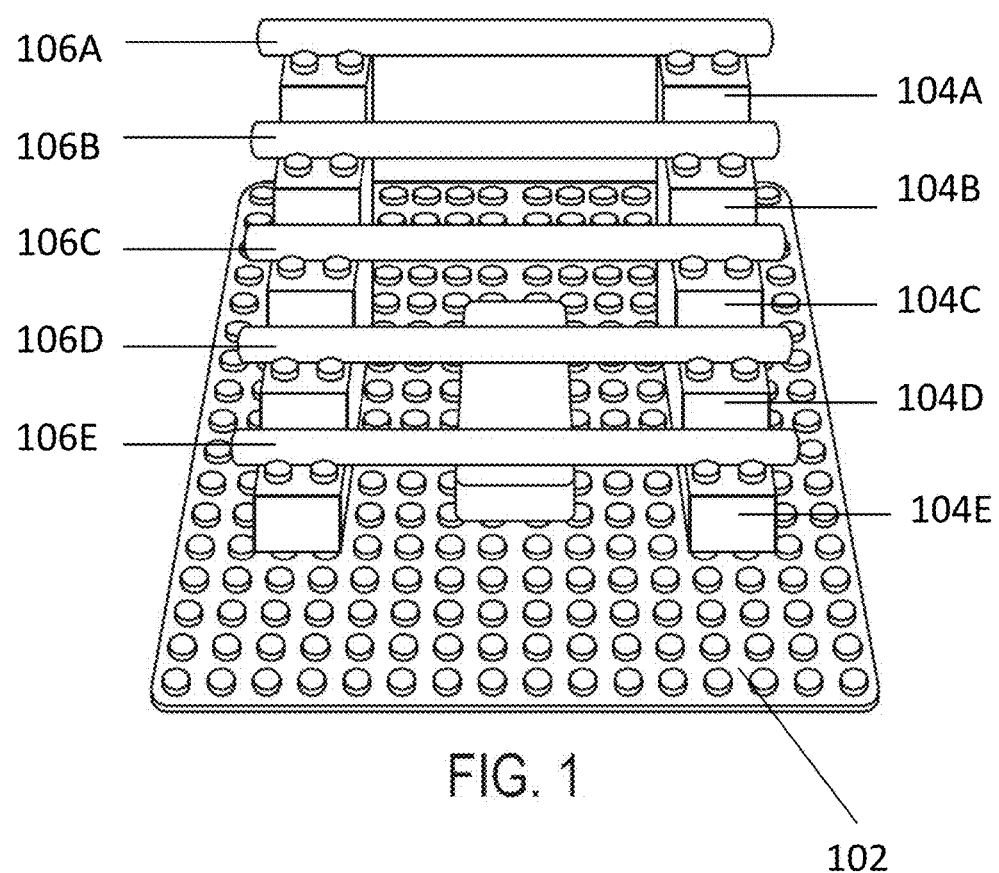
FIG. 1 is an illustration of a rod target model, designed to test a user's movement of a needle or probe within the same initial ultrasound imaging plane, where the user visualizes a cross-section of each rod simultaneously, according to an embodiment of the invention.

The following description recites various aspects and embodiments of the present invention. No particular embodiment is intended to define the scope of the invention. Rather, the embodiments merely provide non-limiting examples of various methods and systems that are at least included within the scope of the invention. The description is to be read from the perspective of one of ordinary skill in the art; therefore, information well-known to the skilled artisan is not necessarily included.

Definition and Abbreviations

The following terms, unless otherwise indicated, shall be understood to have the following meanings:

As used herein, the terms "a," "an," and "the" can refer to one or more unless specifically noted otherwise.

The term "or" is not to be construed as identifying mutually exclusive options. For example, the phrase "X contains A or B" can mean that X contains A and not B, X contains B and not A, or X contains both A and B. That is, the term "or" is used to mean "and/or" unless explicitly indicated to refer to alternatives only or the alternatives are mutually exclusive, although the disclosure may support a definition that refers to only alternatives and "and/or." As used herein "another" can mean at least a second or more.

As used herein, the terms "user," "participant," "examinee," or "trainee" may be used interchangeably and may refer to a person in need of assessment or training for the medical skills related to the methods, apparatus, and systems of the invention described herein.

"Echogenic" or "echoreflective" or "hyperechoic" as used herein all refer to increased sound wave echoes in ultrasonography. By contrast, "hypoechoic" refers to decreased sound wave echoes in ultrasonography. "Echogenic target models" or "target models" as used herein refer to 3-dimensional structural units that are detectable by ultrasound imaging because they reflect ultrasound waves. A target model is generally a modular unit (a module), while "target" may refer to an entire target model unit or a sub-part of a target model. "Echogenic target models," "ultrasound targets," and "target models" are used interchangeably herein.

"Modular" as used herein refers to a design approach that subdivides a system into smaller parts (modules) that can be independently created and then used in different systems to drive multiple functionalities. For example, a variety of target models may be interchangeable within a system that includes a chamber for housing the target models and means for attaching and securing a target model to the chamber (e.g., a pedestal with a magnet embedded inside, which attracts to a second magnet embedded inside a target model, so as to hold the target model in place on the pedestal). Or other types of fasteners may be used.

"Chamber" as used herein refers to the target enclosure and surroundings, including an opaque access surface for contact with an ultrasound probe for imaging. A chamber may be any variety of sizes or shapes to accommodate appropriate targets for simulating various procedures or structures to be accessed.

"Access surface" or "opaque access surface" as used herein refers to the surface through which a user gains access to the target model(s) enclosed within a chamber. The user inserts a needle, probe or other instrument through the opaque access surface to gain access to the target model inside the chamber. The access surface may be opaque such that the user must utilize ultrasound imaging or some other imaging to "see" the target model and needle, probe, or other instruments inside the chamber.

"Geometric access" as used herein refers to the instrument path required to gain access to structures during ultrasound-guided medical procedures. That is, a target model may not be representative of any particular anatomical structure, but gaining access to a particular target on the target model by maneuvering through necessary angles or confined spaces, without contacting any forbidden structures, is an example of gaining geometric access to a target. A "defined geometric access" may refer to the most direct path or a preferred path to a contact surface (target on the target model) without encountering obstacles or non-contact surfaces. A defined geometric access may be one that simulates the access required in a clinical setting.

"Contact surface" as used herein refers to a part of a target model which the user may attempt to contact with the needle, probe, or other instrument as part of a targeting task. That is, a contact surface is an intended target on the target model.

"Non-contact surface" as used herein refers to a part of a target model which the user may attempt to avoid contacting with the needle, probe, or other instrument as part of a targeting task. Any surface not designated as a target or contact surface may be considered a non-contact surface by default. That is, a non-contact surface may be any surface on the target model or chamber that is not an intended target for contact by the user.

Description

Broadly developed skill in ultrasound-guided procedures may be applicable in a wide range of clinical settings. Examples of applications where such training and assessment may be useful include procedures in obstetrics and gynecology, anesthesiology (e.g., regional blocks), interventional radiology, various types of centesis (e.g., arthrocentesis), point-of-care ultrasound procedures, and more. The present invention allows assessment of clinician or preclinical trainee skill in ultrasound-guided procedures. The invention also allows a trainee to develop and improve skill and confidence in essential hand-eye coordination guided by ultrasound imaging in a comfortable setting and without risk to any patient.

In some embodiments, the invention comprises an apparatus for ultrasound-guided procedure assessment and/or training, comprising a 3-dimensional target model component having a plurality of points of contact and access to the points of contact. In some embodiments, the target model component comprises structures positioned at multiple angles. In some embodiments, the target model component simulates common anatomical structures observed in ultrasound-guided procedures. In some embodiments, the apparatus further comprises a chamber component comprising the 3-dimensional target model component and an opaque access surface for contact with an ultrasound imaging system. In some embodiments, the apparatus further comprises a needle or other user-held instrument for performing tasks related to the target model component. The apparatus may further include an ultrasound imaging component for visualizing the target model components and the needle or other user-held instrument via ultrasound probe contact with the chamber access surface.

In some embodiments, the target models of the apparatus are interchangeable within the chamber as a modular system (e.g., using magnets or other fasteners). In some embodiments, the inner surface of the chamber and/or portions of target components are treated with a substance to reduce or enhance echogenicity. Echogenic or echoreflective substances increase visualization of structures—e.g., metal is hyperechoic. By contrast a hypoechoic material (e.g., STYROFOAM®, gel, gelatin, water or some lightweight plastics) may reduce echogenicity.

In some embodiments, the chamber further comprises a fluid in the cavity. The fluid may be water or a more viscous fluid to better represent a specific procedure or anatomical environment through which a needle or other instrument may need to navigate.

In some embodiments, amniocentesis, CVS, or in-utero stent placement may be simulated by the target models placed in the chamber. In other embodiments, the target models may facilitate simulation of thoracentesis, paracentesis, pericardiocentesis, arthrocentesis, percutaneous nephrostomy tube, venous access procedures, abscess or cyst aspiration, or a variety of other procedures.

In other embodiments, the invention comprises a method for assessing skill in ultrasound-guided procedures, comprising: providing an apparatus that comprises a chamber including an opaque access surface and enclosing a 3-dimensional target model component having a contact surface and a defined geometric access to the contact surface; assigning a user a task related to a user-held instrument and the 3-D target model component; and having the user perform the assigned task while visualizing as 2-D or 3-D images the target model component and the user-held instrument via the ultrasound imaging system. The apparatus may include any of the elements described herein. The method may further comprise assigning the user a plurality of tasks related to the target model component. The method may further comprise timing successful performance of the assigned tasks. The method may further comprise comparing the performance of the user to that of experienced and inexperienced clinicians using the same apparatus. The method may further comprise having an experienced examiner (i.e., an individual assessing the user) observe and evaluate performance of an assigned task by the user. The method may further comprise a scoring/timing system where specific performance problems result in a time or score penalty. In some embodiments the user is a clinician having experience with ultrasound-guided procedures. In some embodiments the user is inexperienced with ultrasound-guided procedures.

In other embodiments, the invention comprises a method for training in ultrasound-guided procedures, comprising: providing an apparatus of the invention as described herein; and assigning a user a specific task related to the 3-dimensional target model component. The method may further comprise having the user practice performing the assigned task while visualizing the target model component and the needle or other user-held instrument via the ultrasound imaging system. The method may further comprise assessing and timing user performance of the assigned task. The method may further comprise assigning the user a plurality of tasks related to the target model component.

In some embodiments of each of the methods of the invention, an assigned task is correlated with discrimination between skills of experienced and inexperienced clinicians. In some embodiments, assessment of user skill yields an improved result following practice with the apparatus.

In some embodiments, the invention comprises a system for ultrasound-guided procedure training and assessment, comprising: at least one 3-dimensional target model component; a chamber component for enclosing the 3-dimensional target model component, wherein the chamber comprises the target model component and an opaque access surface for contact with an ultrasound imaging system. The system may further comprise a needle or other user-held component for performing tasks related to the target model component. The system may also comprise an ultrasound imaging system component for visualizing the target model component and the needle or other user-held instrument component via ultrasound probe contact with the access surface. In some embodiments, the at least one target model component comprises structures positioned at multiple angles.

In some embodiments, the system further comprises a detection component for objectively evaluating performance of tasks. The detection component may comprise at least one sensor. In some embodiments, the system may comprise computer readable media for analyzing performance of a user. In some aspects, the sensors and computer readable media may also facilitate unbiased evaluation of user skill. In some embodiments, the system is able to discriminate between experienced clinicians and inexperienced users.

Ultrasound-Guided Procedures

When common ultrasound imaging is utilized, 3-dimensional (3-D) structures are observed in a 2-dimensional (2-D) image on a screen. Efficient use of such 2-D ultrasound images to understand and orient with respect to 3-D physical structures represented in the images is a skill that is challenging to master in a clinical setting. This is, however, a skill that may be improved with practice in a risk-free non-clinical setting. Likewise, even where 3-D images are observed, the user may benefit from practice in a setting where interpretation of depth and direction poses no risk to patients.

Thus, there is a need for an ultrasound-guided skill assessment and training apparatus and system, as well as methods for assessing skill in using ultrasound-guided imaging for procedures, as are described herein. Further provided are training curricula focused on improving a trainee's hand-eye coordination for ultrasound-guided procedures involving a needle or other user-held devices or instruments.

For example, using the apparatuses, methods, and/or systems of the invention, an examinee/trainee may use a probe, needle, or other instrument held in one hand to make contact with target components of a 3-D target model housed within a chamber (container), while simultaneously observing the target via ultrasound using an ultrasound probe held in the other hand and applied to an opaque access surface of the chamber. The examinee/trainee thus experiences the challenges of observing and manipulating a 2-D image while also maneuvering 3-D objects shown in the image.

Echogenic Target Models

In one aspect the claimed invention comprises a 3-D target model for a clinician or pre-clinical trainee to visualize using ultrasound imaging or another type of imaging, while performing an assigned task related to the target model.

In some embodiments the target models include echogenic targets. In some embodiments the shapes or dimensions incorporated in the echogenic targets are inspired by and/or provide a generalized representation of common anatomical structures. In some embodiments, the echogenic targets mimic various anatomical structures and/or a geometric access typically present within the anatomical environment where ultrasound-guided procedures are conducted. Importantly, a target may not physically resemble any particular anatomical structure, but may still present a structure that requires the user to manipulate the needle, probe, guide wire, or other instrument in a way that simulates a particular medical procedure or procedures.

In some embodiments, a target model may be customizable to represent or simulate a specific structure or medical condition. In some embodiments, a target model may be appropriately sized to simulate different sizes of anatomical structures.

As noted herein, in some embodiments, a target model component may be designed to simulate common anatomical structures and/or geometric access observed in ultrasound-guided procedures. "Geometric access" as used herein refers to the instrument path required to gain access to structures during ultrasound-guided medical procedures. In some embodiments, the desired path is the most direct or efficient access path. That is, a target may not be representative of any particular anatomical structure, but gaining access to it by maneuvering through necessary angles or confined spaces, without contacting any forbidden structures (e.g., body parts that could be injured by such contact), is an example of gaining geometric access to the target. Thus, the target may provide not only a "positive" structure that provides a particular orientation, but may also provide a structureless path (i.e., a geometric access) by which preferred access to the structure and/or structures in the target is obtained. Thus, in various embodiments, both the structures and the path are ideally representative of an anatomical environment of interest. For example, for the rod target model shown in FIG. 1, the positive structures may be the horizontal dowel rods, whereas the geometric access may be governed by the positioning of the dowel rods at different levels, thus requiring the user to pursue varied paths to access the dowel rods. Similarly, for the ball target model of FIG. 3, the positive structures are the balls, but the geometric access may be governed by the extensions on which the balls are positioned and the angle and path between the extensions through which the user must negotiate access to the balls.

FIGS. 1-5 demonstrate potential target models according to various embodiments of the invention. FIG. 1 illustrates a rod target model embodiment, designed to test movement between structures within the same ultrasound plane. The initial ultrasound image may advantageously display a plane perpendicular to the long axis of the rods, such that the user visualizes a cross-section of each rod simultaneously. In rod target model 100, a baseplate 102 supports vertical extensions 104A-E having different heights, which in turn support dowel rods 106A-E. This rod target model 100 is designed to test the user's movement of a needle or probe within the same vertical ultrasound imaging plane.

Figure 2:
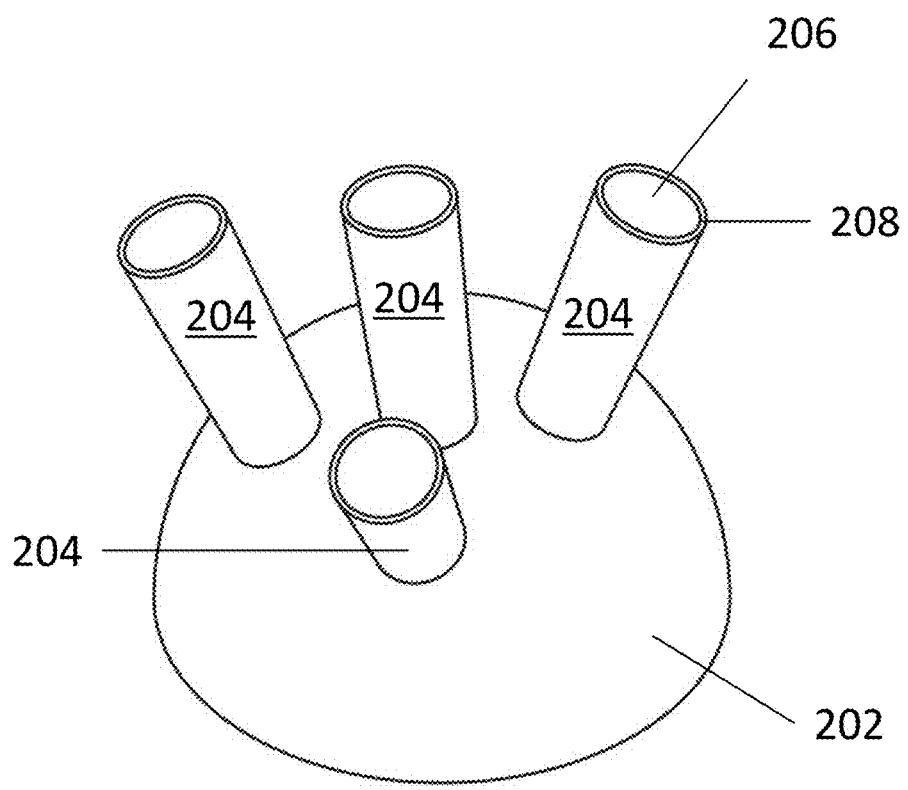
FIG. 2 is an illustration of a straw target model, designed to test a user's movement of a needle or probe while following a restrictive path, such as a path into the lumen of a straw (without touching the sides of the straw), according to another embodiment of the invention.

FIG. 2 illustrates a straw target model embodiment. In straw target model 200, a semi-spherical base 202 supports tubular structures 204, which extend from the base 202 at various angles. This straw target 200 is designed to test movement while following a restrictive path, such as a path into lumen 206 of the straw, without touching the sides 208 of the straw.

Figure 3:
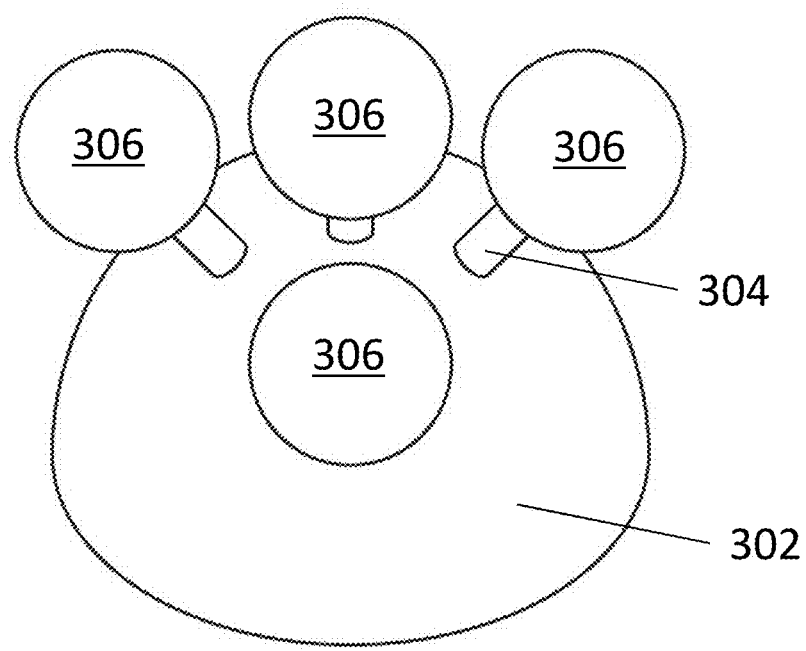
FIG. 3 is an illustration of a ball target model, designed to test a user's guidance/movement of a needle or other instrument to target structures positioned on a non-planar surface not visible via ultrasound in the initial ultrasound image plane, such that the user must adjust the ultrasound probe to visualize the target structures, according to another embodiment of the invention.
Figure 4:
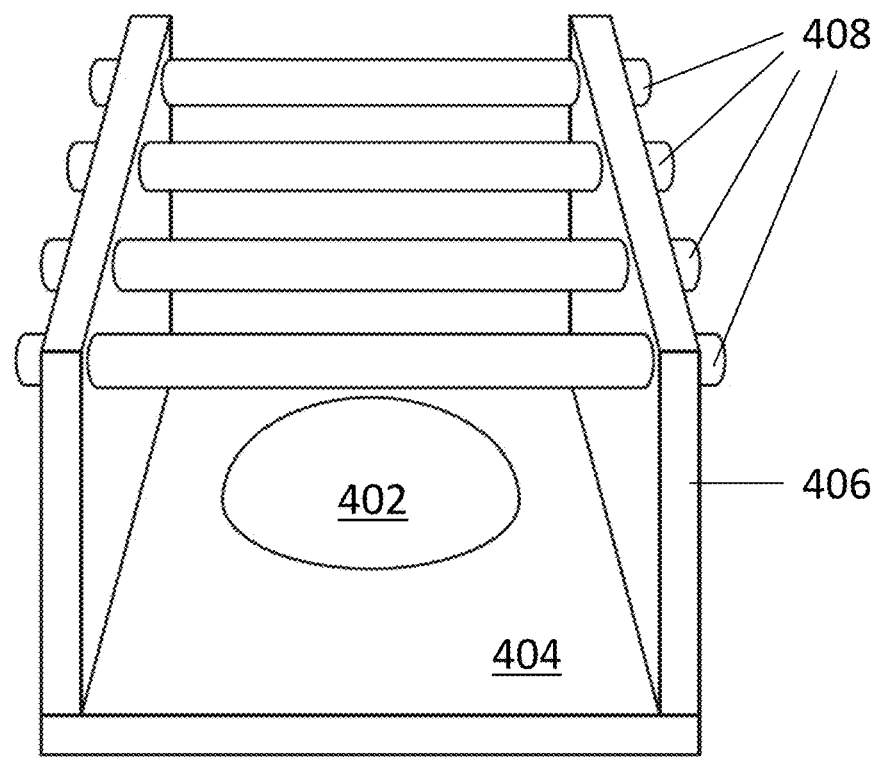
FIG. 4 is an illustration of a rod/ball target model, designed to allow a user access to some target structures (e.g., the ball) only via narrow passages between two other structures, according to another embodiment of the invention.

FIG. 3 illustrates a ball target model embodiment. In ball target model 300, a semi-spherical base 302 supports extensions 304 having rounded (i.e., ball) structures 306 at the distal ends; the distal structures shown are spherical, but they may also be oval or some other shape. This ball target model 300 is designed to test guidance/movement to structures outside the initial ultrasound plane, because the FIG. 4 illustrates a rod/ball target model embodiment. In rod/ball target model 400, a semi-spherical ball structure 402 sits on a rectangular base 404, which also supports two walls 406 with four connecting rods (i.e., dowels) 408 spanning the walls. In this rod/ball target model 400, the ball structure 402 is accessed only via the narrow passages between two rod structures 408.

Figure 5:
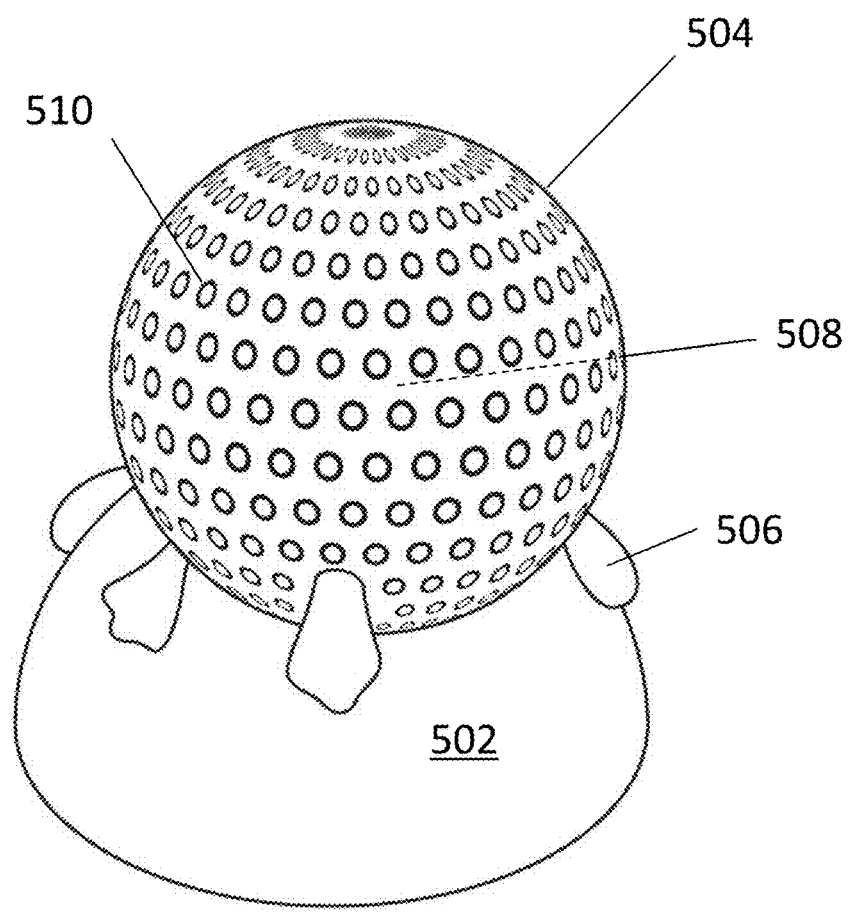
FIG. 5 is an illustration of an aspiration target model, designed to test a user's skill using a needle to withdraw fluid from a mass, according to another embodiment of the invention.

FIG. 5 illustrates an aspiration target model embodiment. In aspiration target model 500, a semi-spherical base 502 supports a fluid-filled mass 504. The mass may have extensions 506 for attachment to the base 502. With this aspiration target model 500, the user may be instructed to use a needle to withdraw fluid 508 from inside the mass 504 via apertures 510. The fluid inside the mass may be dyed a color, such that successful aspiration will yield only the colored fluid.

In some embodiments, portions of the target models may be treated or modified to be more echogenic (e.g., with a particular coating that reflects sound waves to a greater extent than the target would otherwise). For example, in some embodiments, specific target components may be echogenically enhanced for increased reflection of ultrasound waves. For example, a coating of metal, PLASTI DIP®, or some other hyperechoic substance may optimize reflection of sound waves. Conversely, various components may be treated so as to be less echogenic, such as by coating with a substance that increases absorption of ultrasound waves (e.g., STYROFOAM®, gel, gelatin, or some types of lightweight plastic) may reduce echogenicity.

Any number of different materials may be appropriate for constructing the target model components as described herein. For example, components may be made of propylene, polypropylene, polyethylene, aluminum, silicone, variable density silicone or foam material, plaster, ceramic, wood, plastic, stainless steel or other metals or alloys, etc. In some embodiments, a single target model may be comprised of two or more materials.

In some embodiments the target models are interchangeable in a modular fashion within a chamber. In some embodiments two or more target models may be accommodated simultaneously within one chamber.

Needle or Other User-Held Instrument

A user may contact the targets or target model components with a needle, probe, guide wire, or other user-held device or instrument, providing the ability for the user to access (e.g., contact or touch) the target. For example, a typical needle for ultrasound-guided procedures is 3-7 inches long and 17-22 gauge diameter. Alternatively, the user may contact target components with a probe, wand, guide wire, or any other device of sufficient length to reach from the user into the chamber to the contact surfaces of target components.

In some embodiments where the target is housed within a chamber having an access surface for ultrasound imaging, the probe or needle should be long enough to reach the target from an exterior part of a chamber access surface and of sufficient sharpness to pierce or penetrate the access surface of the chamber, which may be made of ballistic gelatin or another suitable access surface substance. The needle or other instrument may be stabilized upon entry into the chamber, as the user views the needle via ultrasound imaging. Thus the user may perform the assigned task while visualizing the target model and the instrument via the ultrasound imaging system while using the instrument to access and penetrate the access surface.

In some embodiments, where aspiration of fluid is an assigned task, the instrument must be capable of withdrawing fluid. A needle, e.g., would be appropriate for aspiration. Specific additional tasks may be designed to require specifically modified instruments, as appropriate. For example, better simulation of certain types of procedures may require the user to traverse the opaque access surface with a guide wire, catheter, drain tube, or other instrument instead of a needle or probe. In some embodiments, a simple probe may be the preferred implement because it does not introduce air bubbles into the surrounding fluid.

In some embodiments, the needle, probe, or other user-held device may be coated or otherwise treated or modified such that it is echogenically enhanced for increased reflection of ultrasound waves. In some embodiments, the needle, probe, or other user-held device may be modified to automatically record touches or contacts, and in some embodiments may also record the accuracy of touches or contacts.

Chamber

The target models described may be housed within an enclosed chamber. Such a chamber may be cylindrical, rectangular, oval, or other shapes, and of variable size and dimensions. The chamber may optionally include a platform or other point of attachment at the base for mounting interchangeable targets. The chamber may be made out of any number of suitable materials, including but not limited to plastics, ceramics, propylene, polypropylene, polyethylene, aluminum, silicone, variable density silicone or foam material, plaster, ceramic, wood, plastic, stainless steel, metals, alloys, or any number of other synthetic materials.

The chamber may generally be opaque, such that a user must visualize the contents of the chamber via ultrasound or some other type of imaging system. The chamber may comprise at least one opaque access surface appropriate for contact with an ultrasound probe to facilitate ultrasound imaging (e.g., 604 and 704). The access surface may also be utilized to access the contents of the chamber with a user-held instrument (e.g., a needle) by penetration of the access surface with the instrument.

For example, in an embodiment the access surface may be made from a ballistic gelatin such as PERMA-GEL® Ballistic Gel (e.g., 10% ballistic gelatin) or another substance with similar pliability, resilience, and optionally self-sealing properties, such that it may be pierced by a needle or other implement or instrument repeatedly and yet maintain its shape and structure. In another embodiment the access surface may be a formed silicone or silicone-type substance, or other substances may be appropriate. The access surface may take a variety of shapes, such as convex, concave, semi-tubular, or flat. For example, in FIG. 6, the access surface 604 is curved and convex. In some embodiments, chamber access surfaces may also be modular (i.e., interchangeable) so as to allow simulation of alternative specific anatomical surfaces. An ideal chamber access surface is self-sealing, resealable, moldable, transmits ultrasound waves, and may have a texture similar to skin.

Figure 6:
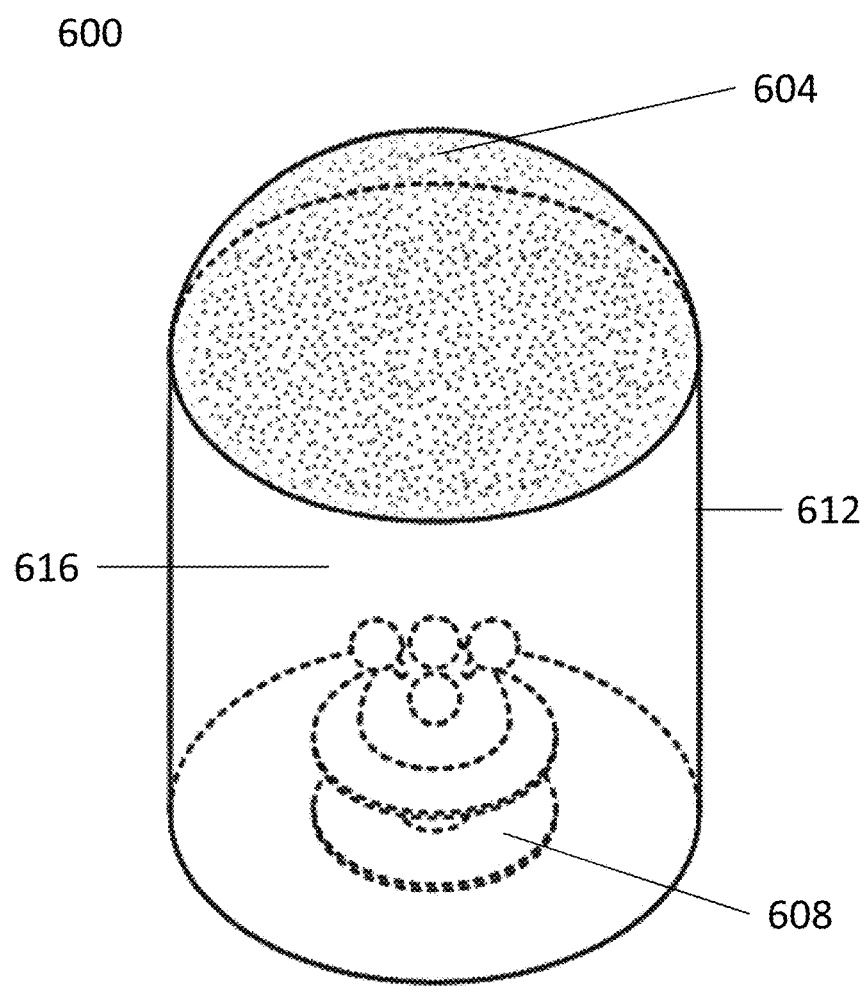
FIG. 6 is an illustration of a cylindrical chamber with a curved opaque access surface, similar to the surface of a distended abdomen, according to an embodiment of the invention.
Figure 7:
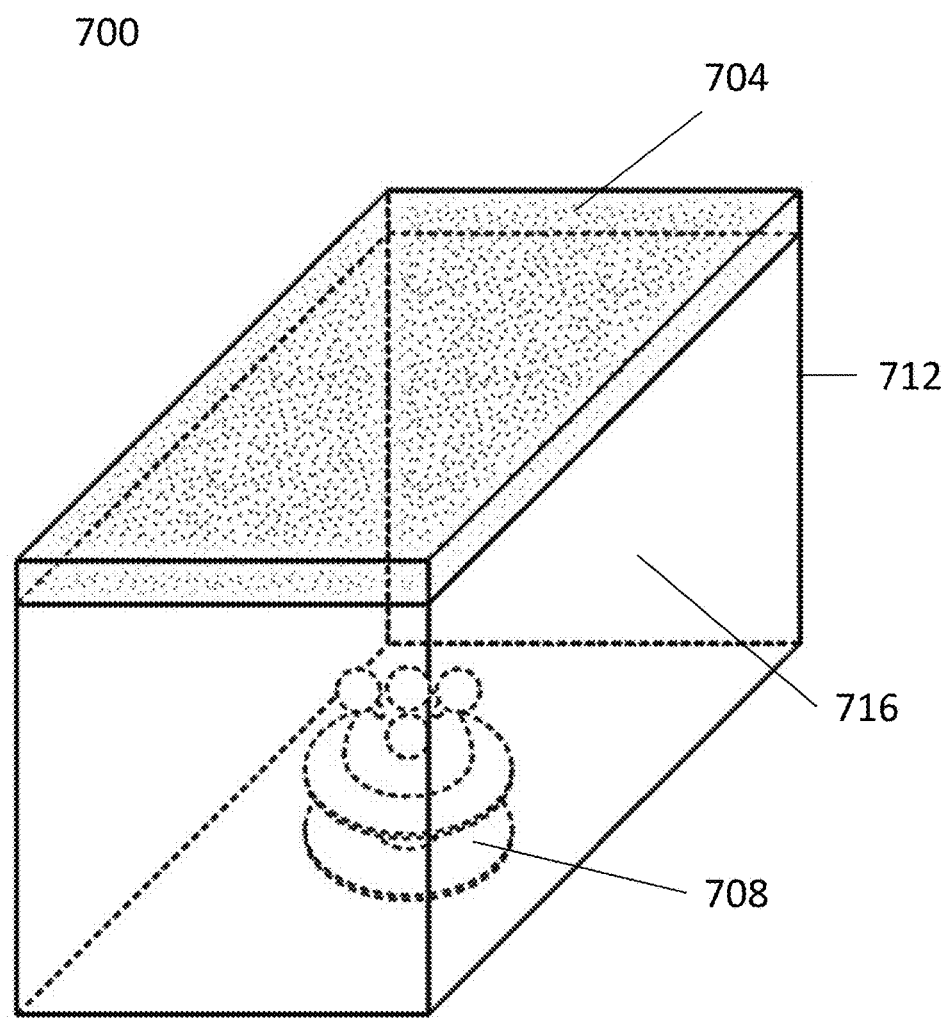
FIG. 7 is an illustration of a rectangular chamber with a flat opaque access surface, according to another embodiment of the invention. The additional space may allow multiple target models to be enclosed in the chamber simultaneously.

FIGS. 6 and 7 illustrate two possible chambers according to embodiments of the invention. FIG. 6 illustrates a cylindrical chamber 600 having cylindrical wall 612 and a curved top opaque access surface 604 made of variable density silicone and/or ballistic gelatin. The target model (shown here, target model 300) may sit on a platform 608 and may be secured by magnets. The curved access surface may resemble a dome or the surface of a woman's abdomen late in pregnancy (i.e., a distended abdomen).

FIG. 7 illustrates a rectangular chamber 700 having a rectangular shape with flat walls 712 and a flat top opaque access surface 704 made of ballistic gelatin. The target model (shown here, target model 300) sits on a platform 708 and is secured by magnets. Although only a single target model is shown, the additional space of the rectangular chamber may allow additional target models to be enclosed in the chamber simultaneously. Alternative orientations of chambers may also be useful for simulating particular procedures. For example, a rectangular chamber may be oriented such that the longer side is vertical. In an apparatus enclosing multiple target models, a user may be assessed for a variety of skills in a single session.

In some embodiments, various materials may be embedded in the surface access (or extended from the surface access or walls of the chamber) so as to more accurately represent anatomy in a real medical procedure. For example, patient ribs could be simulated for thoracentesis procedures by additional solid elements embedded in the opaque surface access.

In some embodiments, the chamber cavity (e.g., 616 and 716) is filled with water. In other embodiments, the cavity may be filled with another suitable substance. For example, the cavity may be filled with a fluid, gel, or other viscous or semi-viscous substance. In some embodiments, the fluid or gel is resistant to accumulation of air bubbles. However, if the user-held device is a probe, wand, or other implement without a lumen or cannula, or without the ability to introduce air bubbles into the fluid or substance, this feature may be unnecessary.

In some embodiments, the inner surfaces of a chamber (e.g., 612 and 712) may be coated with a sound-absorbent material to reduce reflection of ultrasound waves. For example, a layer of STYROFOAM® may be applied as a sound-absorbent coating. In some embodiments, the chamber may be filled or emptied of fluid through a valve on the chamber. Such a valve may be necessary to completely fill the chamber with fluid when the access surface is convex, as where it may be designed to simulate a distended abdomen.

Figure 8:
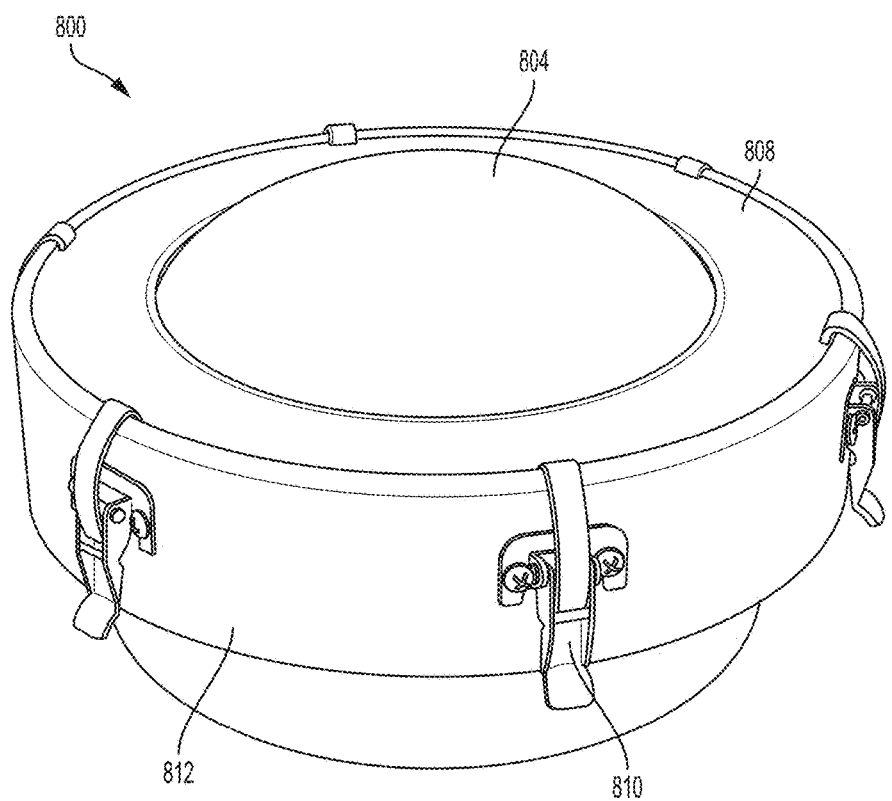
FIG. 8 is an embodiment of a cylindrical chamber having a curved opaque access surface and relatively shallow depth as compared to other embodiments illustrated herein. This chamber was used to test the skill of experienced clinicians as compared to inexperienced ultrasound users.

FIG. 8 is a rendering of a cylindrical chamber as constructed and used for testing experiments. This cylindrical chamber 800 has a cylindrical wall 812 and a curved top access surface 804 made of ballistic gelatin (or variable density silicone). A gasket-type ring 808 and clips or clamps 810 secure the access surface 804 in place. Because the access surface at the top 804 is opaque, the target model is not visible inside the chamber. This cylindrical chamber example is notably shallower in depth than the chamber illustrated in FIG. 6 and therefore may not require a pedestal or platform as illustrated in FIGS. 6 and 7.

Figure 9:
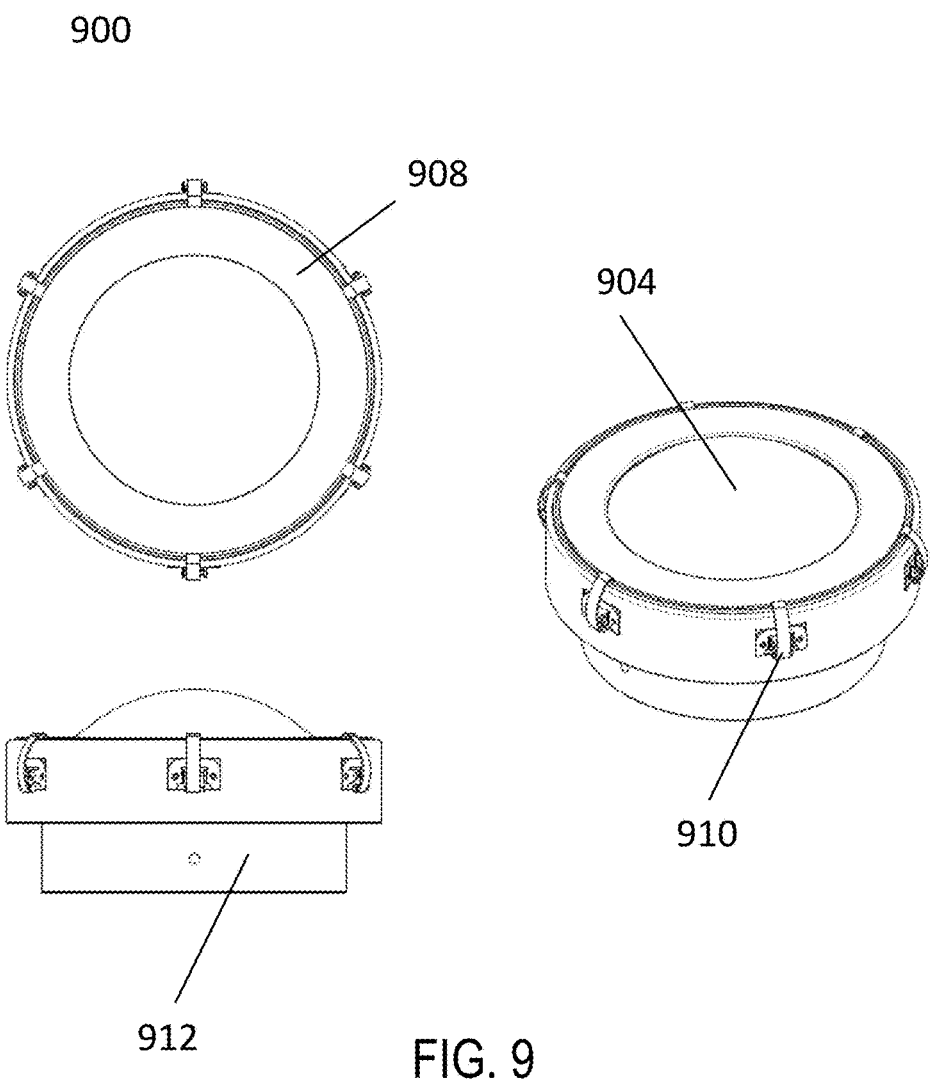
FIG. 9 is an illustration of the cylindrical chamber in FIG. 8 showing three (upper, angular, and side) views.

FIG. 9 is an illustration showing three views of the chamber depicted in FIG. 8. Again, the cylindrical chamber 900 has a cylindrical wall 912 and a curved top access surface 904 made of ballistic gelatin. A gasket-type ring 908 and clips or clamps 910 secure the access surface 904 in place. This chamber was used to compare the skill of experienced clinicians with that of inexperienced ultrasound users, as described in Example 3.

Modular Target Models

In some embodiments multiple target models are interchangeable in a modular fashion within an chamber. For example, in the non-limiting embodiment shown in FIG. 7 structure 708, a platform or pedestal, may comprise a magnet that attracts another magnet embedded within a target model. In such an embodiment, the attraction between magnets secures the target model in place on the platform or pedestal. Or other means of attaching or securing a target model may be used (e.g., fasteners, velcro, screws, etc.). In some embodiments, the platform or pedestal may be adjustable in height, so as to position the target closer to or farther from the ultrasound probe and needle or other user-held device. In some embodiments, additional magnetic or other attachment segments may be stacked on the platform or pedestal before mounting the target, in order to adjust the height of the target. In some embodiments, a single chamber may comprise at least two such platforms for holding multiple targets simultaneously. In some embodiments, a single platform or chamber may be modified to support three or more targets simultaneously.

Any number of different materials may be appropriate substances for constructing the target models, the modular attachment system, and/or the chamber components as described herein. For example, various parts of the apparatus may be made of wood, plastics, metals, variable density silicone or foam material, plaster, ceramic, composites, etc.

Targeting Tasks

In the context of targets enclosed in a chamber as described above, a user (e.g., a clinician or pre-clinical medical professional) may be presented with specific physical targeting tasks in connection with either assessment of skill in ultrasound-guided techniques or for training to improve hand-eye coordination as aided by ultrasound visualization of the target models. In some embodiments, the user may be shown an example of the target model or a target component of the target model, or a picture of the target and a description of the tasks before attempting to perform tasks.

The targeting tasks should require the user to manipulate the needle or other user-held device so as to achieve contact with specific target components (and/or avoid contact with specific target components), while visualizing the needle, probe, guide wire, catheter, drain tube, or other instrument and the target using ultrasound imaging via ultrasound probe contact with the chamber access surface. For example, many users hold a needle with one hand and the ultrasound probe with the other hand, while observing the target structures and the needle or probe on a 2-D computer screen.

Many targeting tasks involve a series of assigned contacts to be made. FIGS. 1-5 illustrate example targets for use in targeting tasks. For example, in FIG. 1, the user may be assigned to touch or contact parts of target 100, such as structure 106A with the needle or probe, and then structure 106B, structure 106C, and so on. Each task may have detailed instructions, and an examiner may supplement those instructions by varying the order of contacts to be made.

In some embodiments, disruption of patterned movements may be desirable. That is, randomizing the order of assigned target contacts may be a more useful training and assessment exercise than contacting components in a logical order that allows minimal adjustment between contacts. For example, in FIG. 1, where rods (dowels) are numbered 106A-E, assigning a more randomized contact order (e.g., B-E-C-A-D) may be more beneficial than simply stepping down from A-E.

Tasks may be designed to require a user to adjust the needle within the same vertical ultrasound plane, acquire an ultrasound image showing two different structures in the same plane, and/or move quickly into a different plane, etc., or other paths may be simulated. In some embodiments, a task may involve avoidance of particular contacts. For example, in FIG. 2 showing straw target model 200, the user may be asked to obtain a longitudinal view of a straw 204 and insert the needle into the lumen 206 of the straw without touching the sides of the straw 208. The initial ultrasound image may display a plane parallel to the straw being targeted. Thus all target straws are not optimally visible at the same time.

In FIG. 3 showing ball target model 300, the user may be directed to contact each of the four balls 306 in a specific order, such that the user is required to adjust the ultrasound probe to allow visualization of the target model in different vertical planes. The user may also be instructed to avoid contact with other parts of the target model 302 and 304. The initial image may display the greatest diameter of a target ball. Thus all target balls are not optimally visible at the same time.

As another example, training using the rod/ball target model 400 (FIG. 4) may require that the semi-spherical ball structure 402 is only accessed via the narrow passages between two rod structures 408. The user may be instructed to contact the ball 402 without touching the rods 408. A cross-section of the rod portions of the target model may provide an optimal starting visual image for the user, or a longitudinal view may be more advantageous.

In some embodiments, such as the FIG. 5 aspiration target 500, the user may be instructed to use a needle to withdraw fluid 508 from a mass 504. FIG. 5 illustrates one target embodiment containing fluid that may be aspirated by the user. The fluid inside the mass may be colored, such that successful aspiration will yield only the colored fluid. The optimal approach to obtaining an initial ultrasound image may vary widely for this target model.

Other targets and tasks may be designed such that the user mimics or replicates the movement and visualization challenges of real ultrasound-guided procedures. For any new target and/or task, performance by experienced clinicians may be compared to performance by inexperienced users of ultrasound imaging. The ability of a particular task to discriminate between experienced clinicians and inexperienced users suggests that task replicates and tests procedural skills already acquired by the experienced participants during their clinical training Thus, practice with such discriminatory tasks is most likely to benefit inexperienced providers.

Many different specific procedures can be simulated by alternating the models housed in the chamber and/or the access surface. In addition to simulation of amniocentesis, CVS, and in-utero stent placement, several other devices and other materials may be placed within the chamber to simulate other ultrasound guided invasive procedure such as: thoracentesis, paracentesis, pericardiocentesis, arthrocentesis, percutaneous nephrostomy tube placement, venous access procedures, abscess or cyst aspiration, or other procedures. In some embodiments, other structures such an organ (e.g., from a cadaver) or even a small animal (e.g., fetal pig) may be placed in the chamber to simulate a particular procedure. Other structures may also be used to simulate procedures.

Detection in Targeting Tasks

In some embodiments, an experienced examiner (e.g., a skilled clinician who is familiar with the apparatus and/or system) may observe a user's performance of targeting tasks to determine success for each task component. The user may also give verbal, visual, or other signals to indicate his or her belief that a particular contact made was correct or incorrect. In some embodiments, target models may be custom-designed to simulate a desired structure or medical condition which may dictate or facilitate evaluation by an observer experienced with the related medical procedures.

In more sophisticated embodiments, the successful performance of targeting tasks may be detectable via one or more components of the target models or chamber or via the user-held instrument. For example, the needle or other user-held device may have a sensor that detects contact with any solid, with any part of the target model, or with some specific target or part of the target. Or, a target model component may be equipped with a sensor for detecting contact made by the needle or other user-held device. Thus, in some embodiments sensors may be pressure-sensitive (i.e., register contact by the user). Thus successful contact with a particular target on the target model may be registered. Additionally or alternatively, a system may include position sensors. For example, position sensors may record the position of a needle, probe, or other instrument or part of an instrument at set time intervals (e.g., every 0.25 seconds). Thus the path of the needle, probe, or other instrument may be tracked and objectively compared to the most direct path (e.g., the defined geometric access).

Electronic Performance Monitoring System

At least one sensor or a series of sensors, either within the chamber, on the procedural device (i.e., needle, probe, catheter, or other instrument), on the operator's hands or gloves, or some combination thereof, may be used to track a user's performance of the various tasks. Positional sensors on a needle, probe, or other instrument may be used to determine the path of a needle or probe (i.e., track the path as the user moves the instrument), while pressure sensors on aspects of the target model may be used to determine whether a target has been contacted with the needle or probe. For purposes of assessing the user's skill, this system may allow for purely objective measures of time and accuracy in performing assigned tasks.

In a training environment this electronic system may present the learner with the target to be touched on a computer screen and may also notify the learner when the correct target has been successfully reached. This process may be repeated, allowing the learner to practice without direct instructor supervision. In the testing/assessment environment, the system may also present the learners with the target to be touched. It may record when each target is touched, and may or may not inform the trainee if an incorrect target was contacted or reached. In addition, the time between contact with each target and the amount of deviation between the user's (i.e., trainee's or examinee's) needle path and an optimal path may be recorded to provide information on the quality of the user's performance on the various tasks.

In some embodiments, various components of the chamber, targets, or needle or probe may be equipped with sensors to detect contact between the needle or other user-held device and correct and/or incorrect components of the targets or chamber. In some embodiments, flashing and/or colored lights or other feedback signals may be used to indicate that the user has made a successful contact with a desired target component or has made contact with a structure that the user was directed to avoid. In some embodiments, the entire path of the needle, probe, or other user-held instrument may be detectable and trackable for a more thorough analysis of user skill.

An optimal path may be the most direct route between the surface access and the target structure, without encountering any obstacle structures. An optimal path may be a "defined geometric access." Deviation from such an optimal path may be quantified using sensor data to assess user skill. This quantification may yield path analysis data which could be incorporated into an objective evaluation of the user. That is, deviation from a defined geometric access may be quantified and incorporated into an objective analysis of the user's performance.

In some embodiments, the performance of a person being assessed may be evaluated in a report. Such a report may include any of the "performance data," such as the values that appear in tables herein, and optionally a report could also illustrate the path of the needle or provide other helpful objective assessment information such as timing. In some embodiments, performance data may be calculated via mathematical manipulations of sensor data. For example, a score may be generated that takes into account a variety of measures of performance based on any or all sensor data gathered during the performance of a given user. In some embodiments, a score or other evaluative measures may be generated automatically. An objective score or other evaluation measure may be generated that does not require human evaluation of performance. Such objective measures may be preferable over human judgment (i.e., subjective evaluation) in some settings. Other system configurations may allow a combination of objective and subjective measures of performance.

In some embodiments, tasks, target models, and targets are compared for their usefulness in discriminating between the skills of experienced clinicians and inexperienced users. Tasks and targets where experienced clinicians perform substantially better than inexperienced users may also indicate usefulness of those tasks and targets for training purposes.

Thus the invention may be embodied in multiple ways, including but not limited to apparatuses, methods, and systems.

In some embodiments, the invention comprises an apparatus for ultrasound-guided procedure assessment or training comprising a 3-dimensional target model component having a contact surface and a defined geometric access to the contact surface. The apparatus may include a plurality of contact surfaces. A plurality of contact surfaces may be positioned at a plurality of different locations on the target model. In some aspects, a portion of the target model may include a non-contact surface structural element that restricts the geometric access to the contact surface.

Some embodiments of the apparatus may include at least one rod as the contact surface. Some embodiments may include at least one cylindrical structure having an opening at one end. The contact surface may be at the distal end of the interior of the cylinder such that the more proximal parts of the interior of the cylinder are non-contact surfaces. Or the contact surface may be on the interior of the cylinder. Some embodiments may include at least one spherical or ovoid structure as the contact surface.

In some embodiments, an apparatus comprising a target model may include at least a portion of the target model filled with a fluid. In certain embodiments the fluid may be accessed with a needle or other user-held instrument.

In some embodiments a portion of the target model and/or chamber may be treated with a substance to alter the echogenicity of the contact surface. Some embodiments of the apparatus further include a detection component. The detection component may be a sensor positioned on a contact surface of the target model.

In some embodiments, an apparatus for ultrasound-guided procedure assessment or training includes a chamber. The chamber may include a 3-dimensional target model component having a contact surface and a defined geometric access to the contact surface. The chamber may also include an access surface, wherein the access surface is sufficiently permeable to allow direct access to the 3-dimensional target model via a user-held instrument. In some embodiments, the access surface is opaque.

A portion of the chamber cavity may be filled with a fluid. In some embodiments of an apparatus according to the invention, alternative modular target models are interchangeable within the chamber via an attachment point positioned inside the chamber. A portion the interior of the chamber may be treated with a substance to alter the echogenicity of the contact surface.

In some aspects, an apparatus comprising a chamber and a 3-D target model may include a plurality of different contact surfaces on the target model. Some embodiments may include at least one rod as the contact surface. Some embodiments may include at least one cylindrical structure having an opening at one end. The contact surface may be at the distal end of the interior of the cylinder and the more proximal parts of the interior of the cylinder may be non-contact surfaces. Or some part of the interior of the cylinder may comprise a contact surface.

Some embodiments include at least one spherical or ovoid structure as the contact surface. A target model may include at least a portion of the target model filled with a fluid, such that the fluid may be accessed with a needle or other user-held instrument. If the chamber is also filled with a fluid, the target model or portion of the target model may be filled with a different fluid. In some aspects a portion of the target model may include a non-contact surface structural element that restricts the geometric access to the contact surface.

In other aspects, a portion of a contact or non-contact surface may be treated with a substance to alter the echogenicity of the surface. The interior walls of the chamber may also be treated to alter echogenicity. In some embodiments, an apparatus comprising chamber and a 3-D target model may further include a sensor positioned on the target model, and/or on a needle or other user-held instrument, and/or on the hand or glove of the user.

Some embodiments of the apparatus further include a detection component. The detection component may be a sensor. In some embodiments, an apparatus comprising a chamber and a 3-D target model may further include a sensor positioned on the target model, and/or on a needle or other user-held instrument, and/or on the hand or glove of the user. The sensor may allow detection of contact with parts of the target model and/or tracking of the path of a needle or other user-held instrument.

The invention may also be embodied as a method for assessing skill in ultrasound-guided procedures. The method may include steps of providing a 3-dimensional target model component having a contact surface and a defined geometric access to the contact surface enclosed within a chamber, an ultrasound and imaging system, and a user-held instrument for accessing the contact surface. The method may further include assigning a user a task related to accessing the contact surface. The method may also include having the user perform the assigned task while visualizing the target model and the instrument via the ultrasound imaging system to access and penetrate the contact surface using the instrument.

In some embodiments, where the method includes assigning tasks related to a target model, the user may be assigned the task of contacting a particular contact surface on a target model, by using the user-held instrument. The method may include confirmation of contact with a contact surface. The user may be instructed not to contact other structures, the non-contact surfaces. If a user contacts a non-contact surface, a penalty may be assessed in evaluation of user performance.

A method according to the invention may further include comparing the performance of the user to that of experienced and inexperienced clinicians using the same apparatus to perform the same assigned tasks related to a target model. The target model may be any of the embodiments described herein. For example, the target model may include a rod, and/or a cylindrical structure, and/or a spherical or ovoid structure, and/or a fluid-containing structure. In some embodiments, correct or incorrect performance of tasks may be detected by an observer or automatically and may generate a time or score penalty. In some methods, a portion of a contact or non-contact surface may be treated with a substance to alter the echogenicity of the surface. The interior walls of the chamber may also be treated to alter echogenicity.

Some embodiments of the apparatus used in the method further include a detection component. The detection component may be a sensor. In some embodiments, an apparatus comprising a chamber and a 3-D target model may further include a sensor positioned on the target model, and/or on a needle or other user-held instrument, and/or on the hand or glove of the user. The sensor may allow detection of contact with parts of the target model and/or tracking of the path of a needle or other user-held instrument.

In other embodiments, the invention may comprise a system for ultrasound-guided procedure assessment or training The system may include a 3-dimensional target model component having a contact surface and a defined geometric access to the contact surface. The system may also include a chamber component for enclosing the target model. The chamber may comprise an access surface. The system may also include an ultrasound imaging system (or another imaging system) for visualizing the target model via the access surface. The access surface may be sufficiently permeable to allow direct access to the 3-dimensional target model via penetration of the access surface by a user-held instrument. In some embodiments, the cover or access surface of the chamber may be constructed from ballistic gelatin and/or other materials such as silicone rubber. The access surface may mimic the density, thickness, ultrasound appearance, tactile feel upon palpation and upon needle insertion and advancement, and resistance similar to the human body wall. In some embodiments, a system may be modified to simulate a particular medical procedure. The target model and/or chamber and/or surface access and/or user-held instrument may be varied to better simulate a specific procedure. Some embodiments may simulate amniocentesis or another type of centesis.

In some aspects, a system of the invention may further include a detection component. The detection component may include at least one sensor. The sensor may be positioned on the target model, and/or on a needle or other user-held instrument, and/or on the hand or glove of the user. The sensor may allow detection of contact with parts of the target model and/or tracking of the path of a needle or other user-held instrument. In some embodiments, automatic detection of correct and/or incorrect performance of tasks may be used in objective evaluation of user performance. Incorrect or inefficient performance may generate a time or score penalty.

In some embodiments, systems may further include computer readable media. The computer readable media may allow objective evaluation of user skill. The objective evaluation may include timing, correct contact with contact surfaces, tracking of the user-held instrument and quantification of deviation from a defined geometric access, or other factors. In some embodiments, user performance may be compared with performance of experienced and inexperienced users performing the same targeting tasks. In some embodiments, performance of users having practiced ultrasound-guided procedures with the system may be compared to performance of users who have not practiced with the system.

In some systems, the inner surface of the chamber and/or portions of target model components may be treated with a substance to alter echogenicity. In some systems, modular alternative target model components may be interchanged via a common attachment point. In some embodiments, systems may include target models having a rod, a cylindrical structure, a spherical or ovoid structure, and/or a fluid-containing structure. In some methods, a portion of a contact or non-contact surface may be treated with a substance to alter the echogenicity of the surface. The interior walls of the chamber may also be treated to alter echogenicity.

EXAMPLES

Example 1

Targeting Tasks

Figure 10:
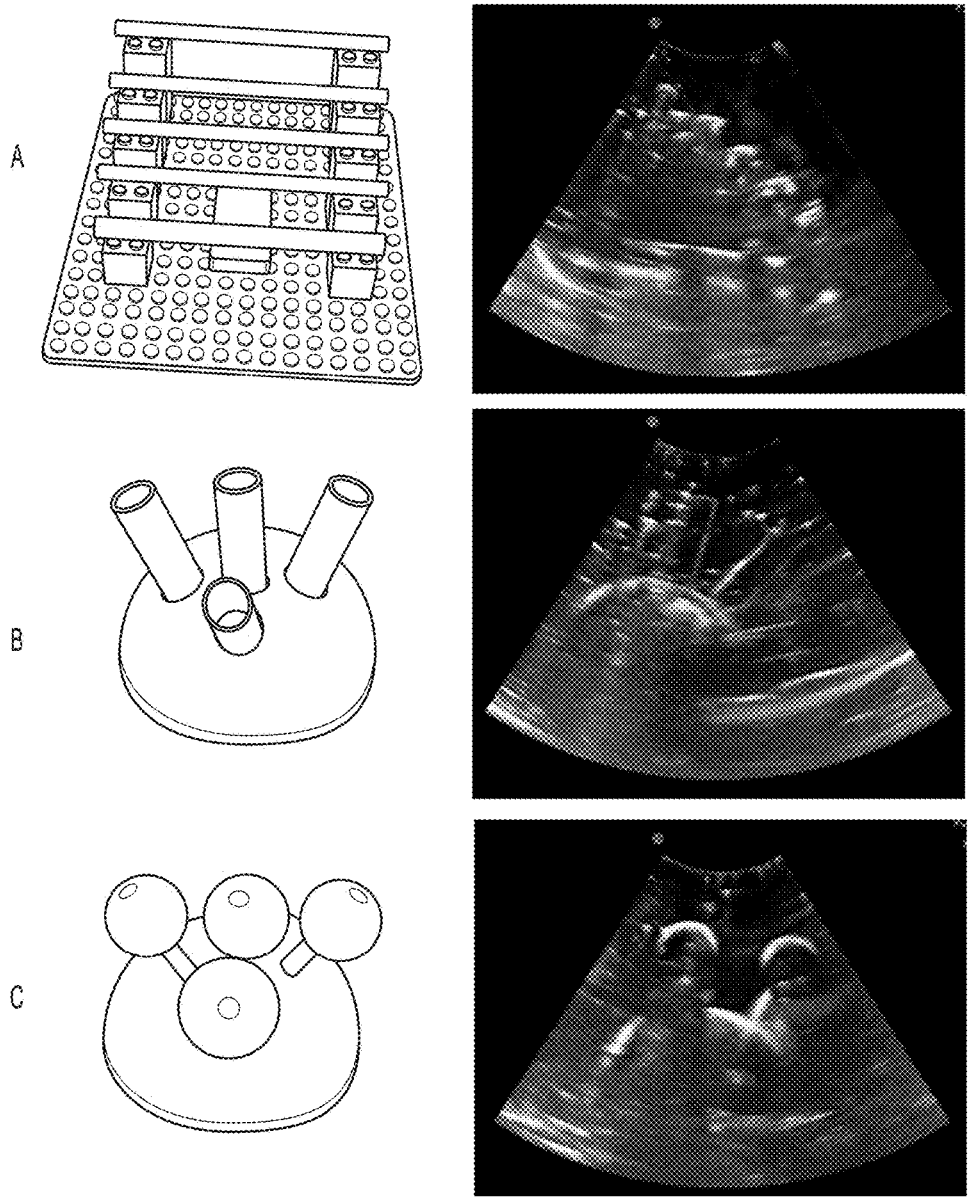
FIG. 10 demonstrates example ultrasound images for the rod, straw, and ball target models, where panel 10A is the rod target model (left) and corresponding ultrasound image (right), panel 10B is the straw target model (left) and corresponding ultrasound image (right), and panel 10C is the ball target model (left) and corresponding ultrasound image (right).

Three target models using wooden dowel rods (100), drinking straws (200), and wooden balls (300) as ultrasound targets were constructed and used in three distinct targeting tasks. FIG. 10 demonstrates example ultrasound images in the right column for each of the three target models in the left column—dowel rod target model 100 in panel A, straw target model 200 in panel B, and ball target model 300 in panel C. The rod task (FIG. 10A) required participants to obtain a cross-sectional view of all rods and touch each rod in series a total of 5 times while adjusting the needle path within the same vertical ultrasound plane without removing the needle. The straw task (FIG. 10B) required participants to follow a restrictive path while placing the needle into each straw in series a total of 3 times while removing the needle each time. The ball task (FIG. 10C) required participants to touch each ball in series a total of 3 times each time adjusting the needle path to a target outside the initial ultrasound plane without removing the needle. Completion time and targeting errors were recorded for residents (n=11), fellows (n=3), and faculty (n=3). A 5-second penalty was assessed for each error. Performance was compared between those with experience in needle guided procedures (fellows and faculty) to those without experience (residents) using a Mann-Whitney U test.

Rod Task (FIG. 1 and FIG. 10, Panel A)

The dowel rod closest to the bottom of the trainer was designated rod #1 and the highest dowel rod was designated rod #5. See, e.g., FIG. 1, 106A-E. The participant (examinee) was asked to obtain a cross-sectional image of the dowel rod target model and asked to touch rod #1. Without removing the needle the examinee was instructed to adjust the needle within the vertical ultrasound plane and perform thirty additional touches of the rods in a random order as directed by the examiner. A penalty of 5 seconds was assessed if the rod was missed or the length of the needle left the ultrasound view for more than 3 seconds.

Straw Task (FIG. 2 and FIG. 10, Panel B)

Each of the four straws were designated as the appropriate "bases" as they would be located on a baseball diamond. See FIG. 2, 204. The examinee was asked to obtain a longitudinal view of a straw and insert the needle into the lumen 206 of the straw without touching the sides 208. Removing the needle from the trainer each time, the examinee was instructed to insert the needle into the straws 10 additional times in a random order as directed by the examiner. A penalty of 5 seconds was assessed if the straw lumen 206 was missed, the wall of the straw 208 was touched, or the length of the needle left the ultrasound view for more than 3 seconds.

Ball Task (FIG. 3 and FIG. 10, Panel C)

Each of the four balls were designated as the appropriate "bases" as they would be located on a baseball diamond. See FIG. 3, 306. The examinee was asked to obtain an image of home and $2^{nd}$ base in the same ultrasound image and asked to touch home. Without removing the needle the examinee was instructed to adjust the ultrasound plane to obtain an image of 20 additional target components in a random order as directed by the examiner, move the needle into that plane, and touch the desired target component. A penalty of 5 seconds was assessed if the ball was missed or the length of the needle left the ultrasound view for more than 3 seconds.

Results

All participants indicated that the tasks would allow for the practice of targeting skills and aid in training Preliminary results with a first set of target models are presented in Table 1. These experiments showed no differences between the experienced and inexperienced groups on either the rod or straw tasks. Experienced providers performed significantly better than the inexperienced group in the ball task, as shown in the "Task Performance" table below (p<0.05). Thus, although the rod and straw tasks did not discriminate, the ball task clearly showed benefit of prior experience. The ball task was therefore considered likely to be helpful in training, and additional tasks with good discriminatory ability were considered.

TABLE 1

| Task | Inexperienced (n = 11) | Experienced (n = 6) | p-value |
|---|---|---|---|
| Rod Task | | | |
| Time (sec) | 231 +/− 30 | 203 +/− 42 | >0.05 |
| # Errors | 15.5 +/− 2.2 | 12.2 +/− 0.8 | >0.05 |
| Adj Time (sec) | 308 +/− 35 | 263.8 +/− 44 | >0.05 |
| Straw Task | | | |
| Time (sec) | 225 +/− 27 | 248 +/− 59 | >0.05 |
| # Errors | 6.6 +/− 1.3 | 5.0 +/− 1.1 | >0.05 |
| Adj Time (sec) | 258 +/− 32 | 273 +/− 57 | >0.05 |
| Ball Task | | | |
| Time (sec) | 271 +/− 23 | 189 +/− 20 | 0.04 |
| # Errors | 10.9 +/− 0.8 | 6.8 +/− 1.5 | 0.04 |
| Adj Time (sec) | 325 +/− 26 | 223 +/− 27 | 0.02 |

After preliminary results were obtained, the rod and straw tasks did not appear to discriminate between experienced clinicians and inexperienced ultrasound users, but the ball task clearly showed benefit of prior experience. The ability of the ball task to discriminate between users based on experience suggested that it may replicate procedural skills already acquired by the experienced participants during their clinical training Thus, repetitions with this task were considered likely to benefit inexperienced providers.

Although the rod and straw tasks did not discriminate in a preliminary study of this particular sample of users, the focus of those tasks, in plane needle adjustment and restricted needle path guidance are also considered important guidance skills. Modifications of these tasks or development of new tasks that focus on these guidance skills were expected to show good discriminatory ability and provide additional tasks that will benefit ultrasound needle guidance training Moreover, the clinical performance of trainees may be compared to the performance of inexperienced clinicians not having the benefit of such training Again, the targets and/or tasks showing the most discriminatory ability may be most likely to provide useful training and assessment exercises.

EXAMPLE 2

Target Model and Apparatus Construction

Rod Target Model

Two sets of five steps were made with LEGO® blocks measuring 3⅛ inches long and ⅝ inches wide. The first step was ⅝ inches long, ⅝ inches wide, and ⅜ inches high, with each of the remaining four steps measuring ⅜ inches higher than the preceding step. The two sets of steps were placed 3¾ inches apart on a LEGO® baseplate measuring 5 inches×5 inches. One-quarter inch diameter wooden dowels were cut to 3¾ inch length and glued to the LEGO® steps on each end (the rods). An all-purpose magnet (lift capacity 3 lbs.) was then glued to the top of the LEGO® baseplate. The entire dowel rod target model was then sprayed with PLASTI DIP® for waterproofing.

Straw Target Model

A 3 inch diameter STYROFOAM® ball was cut in half to create a hemisphere. Four 1 cm diameter drinking straws were then placed into the convex side of the hemisphere at different angles in a baseball diamond configuration. An all-purpose magnet (lift capacity 3 lbs.) was then embedded in the flat side of the hemisphere. A 3 inch diameter piece of thin plastic was then attached to the flat side of the hemisphere with silicone caulk. The entire straw target model was then sprayed with PLASTI DIP® for waterproofing.

Ball Target Model

A 3 inch diameter STYROFOAM® ball was cut in half to create hemisphere. A 3/16 inch wooden dowel was placed into the central hole of a ½ diameter spherical wooden bead. Four such dowel/bead constructs were made. The dowel end of the four constructs was inserted into the convex side of the STYROFOAM® hemisphere at different angles in a baseball diamond configuration. An all-purpose magnet (lift capacity 3 lbs.) was then embedded in the flat side of the hemisphere. A 3 inch diameter piece of thin plastic was then attached to the flat side of the hemisphere with silicone caulk. The entire ball target model was then sprayed with PLASTI DIP® for waterproofing.

Rod/Ball Target Model

A box measuring 4 inches long, 3 inches wide, and 2 inches tall with the top and both 3 inch sides left open was constructed from ⅛ inch plywood. A one inch diameter foam ball was then cut in half to create a hemisphere. The flat side of the hemisphere was then glued in the center of the bottom of the plywood box. An all-purpose magnet (lift capacity 3 lbs.) was glued to the underside of the bottom of the box. Four ¼ inch diameter wooden dowel rods were placed ⅞ inches apart across the top of width of the box (rods). The entire rod/ball target model was then sprayed with PLASTI DIP® for waterproofing.

Aspiration Target Model

A 2 inch high and 3 inch diameter STYROFOAM® cylinder was created. An all-purpose magnet (lift capacity 3 lbs.) was then embedded in one end of the cylinder. A 3 inch diameter piece of thin plastic was then attached to the cylinder over the magnet with silicone caulk. A 2 inch diameter and 1 inch deep piece was cut out of the top of the cylinder. The STYROFOAM® cylinder was then sprayed with PLASTI DIP® for waterproofing. The air was removed from a 3 inch diameter air-filled, spherical, flexible silicone child's toy and replaced with colored water. The now water-filled toy was then glued to the top of the STYROFOAM® cylinder.

Chamber Assembly

A cylindrical plastic container was constructed, 9 inches in diameter and 9 inches tall, to form the outer vessel or "chamber" for the target apparatus. A ring of ⅛ inch wood with an outer diameter of 13 inches and inner diameter of 9 inches was cut and sprayed with FLEXI-SEAL® for water proofing. After the FLEXI-SEAL® dried, the ring was glued to the top of the plastic container. A 7/32 inch diameter hole was drilled into the side of the container 2 inches from the bottom. A one-way LUER-LOK® syringe port was then inserted into the hole. A layer of STYROFOAM® or other sound absorbing material was placed at the bottom of the container. A round piece of PERMA-GEL® Ballistic Gel, ⅜ inch thick×13 inches in diameter, dyed with acrylic peach/flesh-colored paint, was used as the chamber access surface. The ballistic gel simulated synthetic skin and was placed on top of the wooden ring. A second ⅛ inch wooden ring was cut with an outer diameter of 13 inches and inner diameter of 10 inches. The second ring was placed on top of the ballistic gel. Spring clamps were then placed around the periphery of the vessel holding the ballistic gel between the two wooden rings.

A 1⅛ inch high platform was constructed from 2 inch diameter PVC pipe. A stack of all-purpose magnets (lift capacity for each 3 lbs.) was placed within the PVC pipe and the platform held to the bottom of the container by placing an additional magnet underneath the container. The different targeting models were then easily interchanged by placing the magnet within the models on the platform, in modular fashion. The container was filled with water and covered with a ballistic gelatin. The top wooden ring was then placed upon the gelatin and held in place with spring clamps. Additional water was added to the container as needed using a LUER-LOK® syringe port positioned 2 inches from the bottom of the chamber (not shown in Figures). Any air trapped within the container was removed using a needle and syringe to aspirate the air. Sonographic gel was then placed upon the ballistic gelatin access surface and an ultrasound probe used to visualize the echogenic targets in the different targeting models.

Example 3

Testing with Redesigned Apparatus and System

Experiments conducted with a redesigned system yielded slightly different results. The rod, straw, and ball targeting models and cylindrical chamber were constructed as described in Example 2.

The cylindrical chamber shown in FIGS. 8 and 9 was constructed as a redesigned prototype. The base of the chamber was machined from acetal resin plastic, the surface access was made from silicone rubber, and the retaining ring (gasket-like) was made from machined aluminum. This prototype was used to test the skill of a new set of experienced clinicians as compared to inexperienced ultrasound users. This chamber is bigger than the enclosures initially used for the preliminary studies (data in Table 1) but also substantially shallower than the chambers depicted in FIGS. 6 and 7.

Testing with the redesigned system clearly demonstrated differences between experienced clinicians and inexperienced ultrasound users. Results are shown in Table 2. In the Table 2 dataset, only the straw task demonstrated a significant difference between groups in the unadjusted completion time. However, the number of errors and adjusted completion time were significantly lower in the experienced provider group for all three tasks ($p<0.05$).

TABLE 2

| Task | Inexperienced (n = 14) | Experienced (n = 5) |
|---|---|---|
| Rod Task | | |
| Time (sec) | 233 +/− 67 | 205 +/− 45 |
| # Errors | 20 +/− 5.7 | 7 +/− 4.5* |
| Adj Time (sec) | 330 +/− 70 | 238 +/− 65* |
| Straw Task | | |
| Time (sec) | 276 +/− 63 | 205 +/− 62* |
| # Errors | 11 +/− 3.6 | 2 +/− 1.4* |
| Adj Time (sec) | 330 +/− 71 | 215 +/− 61* |
| Ball Task | | |
| Time (sec) | 256 +/− 62 | 201 +/− 38 |
| # Errors | 15 +/− 5.8 | 4 +/− 2.4* |
| Adj Time (sec) | 329 +/− 67 | 223 +/− 50* |

*$p < 0.05$

The invention claimed is:

1. An apparatus comprising:
   a user-held device;
   an ultrasound imaging system comprising an ultrasound probe and a two-dimensional display, wherein the two-dimensional display is configured to display a two-dimensional visual image of objects detected by the ultrasound probe;
   a three-dimensional target model component having an echogenicity, which comprises a contact surface, wherein the three-dimensional target model component further comprises a first sensor disposed on the contact surface, wherein the first sensor is configured to detect contact by the user-held device; and
   a chamber, which comprises an interior cavity having one or more interior surfaces and configured to enclose the three-dimensional target model component, and which further comprises an opaque access surface that is also configured to permit penetration from an exterior of the chamber into the interior cavity of the chamber by the user-held device and to transmit ultrasonic waves, wherein the one or more interior surfaces are coated with a sound-absorbent material, and wherein at least a portion of the three-dimensional target model component is treated with a substance to alter the echogenicity of the contact surface.

2. The apparatus of claim 1, wherein the three-dimensional target model component comprises a plurality of contact surfaces.

3. The apparatus of claim 1, wherein the three-dimensional target model component comprises a rod, a cylindrical structure having an opening at one end, a spherical or ovoid structure, or a structure having at least a portion filled with a fluid.

4. The apparatus of claim 1, wherein the interior cavity of the chamber comprises a fluid.

5. The apparatus of claim 1, wherein the user-held device comprises a second sensor.

6. A method for assessing skill in ultrasound-guided procedures, comprising:
   providing the apparatus of claim 1 to a user;
   assigning the user a task related to accessing the contact surface of the three-dimensional target model component with the user-held device; and
   having the user perform the task while observing the three-dimensional target model component using the two-dimensional display.

7. The method of claim 6, further comprising comparing a performance of the user to that of an experienced user or an inexperienced user using the apparatus to perform the task.

8. The method of claim 6, further comprising automatically detecting a correct or an incorrect performance of the task.

9. The apparatus of claim 1, wherein the user-held device is a needle, a probe, or a guide wire.

10. The apparatus of claim 1, wherein the chamber comprises a platform for mounting the three-dimensional target model component.

11. The apparatus of claim 1, wherein the access surface is comprised of a self-sealing material.

12. The apparatus of claim 5, wherein the second sensor comprised by the user-held device is a position sensor.

* * * * *